US011332862B2

(12) United States Patent
Burgess et al.

(10) Patent No.: US 11,332,862 B2
(45) Date of Patent: May 17, 2022

(54) LOW LINTING IMAGED HYDROENTANGLED NONWOVEN COMPOSITE

(71) Applicant: AVINTIV Specialty Materials Inc., Charlotte, NC (US)

(72) Inventors: Steven Brian Burgess, Troutman, NC (US); Jerry Snider, Mooresville, NC (US); Paul Michael Harmon, Troutman, NC (US); Dianne B. Ellis, Cary, NC (US)

(73) Assignee: AVINTIV Specialty Materials Inc., Charlotte, NC (US)

( * ) Notice: Subject to any disclaimer, the term of this patent is extended or adjusted under 35 U.S.C. 154(b) by 162 days.

(21) Appl. No.: 15/211,326

(22) Filed: Jul. 15, 2016

(65) Prior Publication Data
US 2017/0016158 A1    Jan. 19, 2017

Related U.S. Application Data

(60) Provisional application No. 62/192,698, filed on Jul. 15, 2015.

(51) Int. Cl.
*D04H 1/492* (2012.01)
*B32B 5/26* (2006.01)
(Continued)

(52) U.S. Cl.
CPC ............ *D04H 1/492* (2013.01); *A61F 13/00* (2013.01); *B32B 3/30* (2013.01); *B32B 5/02* (2013.01);
(Continued)

(58) Field of Classification Search
CPC .......... D04H 1/498; D04H 1/49; D04H 1/593; D04H 1/492; D04H 1/48; D04H 1/485;
(Continued)

(56) References Cited

U.S. PATENT DOCUMENTS 3,683,921 A   8/1972  Brooks et al.
6,314,627 B1  11/2001 Ngai
(Continued)

FOREIGN PATENT DOCUMENTS

EP    0418493 A1    3/1991
EP    1813167 A1    8/2007
(Continued)

OTHER PUBLICATIONS

International Search Report and Written Opinion of corresponding International Application No. PCT/US2016/042476, dated Sep. 28, 2016, all enclosed pages cited.
(Continued)

*Primary Examiner* — Peter Y Choi
(74) *Attorney, Agent, or Firm* — Burr & Forman LLP

(57) ABSTRACT

Hydroentangled composites having a wide variety of uses (e.g., personal hygiene articles, facers for fenestration absorbent patches on surgical drapes, facers on absorbent surgical drapes, etc.) are provided. The hydroentangled composite includes at least two nonwoven webs hydroentangled together. The hydroentangled composite may have a three-dimensional structure. Additionally, the at least two nonwoven webs may have different bonding levels and/or lint levels.

14 Claims, 5 Drawing Sheets

(51) Int. Cl.
*B32B 5/02* (2006.01)
*D04H 1/498* (2012.01)
*D04H 1/485* (2012.01)
*D04H 3/14* (2012.01)
*B32B 5/08* (2006.01)
*B32B 7/12* (2006.01)
*B32B 5/06* (2006.01)
*B32B 3/30* (2006.01)
*B32B 7/05* (2019.01)
*A61F 13/00* (2006.01)
*B32B 37/20* (2006.01)

(52) U.S. Cl.
CPC ............... *B32B 5/022* (2013.01); *B32B 5/06* (2013.01); *B32B 5/08* (2013.01); *B32B 5/26* (2013.01); *B32B 7/05* (2019.01); *B32B 7/12* (2013.01); *B32B 37/20* (2013.01); *D04H 1/485* (2013.01); *D04H 1/498* (2013.01); *D04H 3/14* (2013.01); *B32B 2250/20* (2013.01); *B32B 2262/0253* (2013.01); *B32B 2262/0276* (2013.01); *B32B 2262/12* (2013.01); *B32B 2262/14* (2013.01); *B32B 2305/20* (2013.01); *B32B 2307/40* (2013.01); *B32B 2307/4023* (2013.01); *B32B 2307/50* (2013.01); *B32B 2307/54* (2013.01); *B32B 2307/554* (2013.01); *B32B 2307/718* (2013.01); *B32B 2307/726* (2013.01); *B32B 2307/728* (2013.01); *B32B 2307/75* (2013.01); *B32B 2310/0409* (2013.01); *B32B 2432/00* (2013.01); *B32B 2555/02* (2013.01)

(58) Field of Classification Search
CPC . D04H 3/11; D04H 3/05; D04H 18/04; D04H 1/495; D04H 1/558; Y10T 442/671; Y10T 442/489; Y10T 428/249922; Y10T 442/689; Y10T 442/663; Y10T 442/60; Y10T 442/659; Y10T 442/637; Y10T 442/66; Y10T 442/668; Y10T 442/641; Y10T 428/2929; B32B 27/12; B32B 5/022; B32B 5/26; B32B 2250/20; B32B 5/06; A61F 2013/15902; A61F 2013/15934; A61F 2013/15959; A61F 2013/15983; A61F 2013/15991
USPC ....... 442/381, 283, 284, 392, 401, 408, 361, 442/382, 387
See application file for complete search history.

(56) References Cited

U.S. PATENT DOCUMENTS

| | | | |
|---|---|---|---|
| 6,430,788 B1* | 8/2002 | Putnam | D04H 3/105 28/104 |
| 6,503,855 B1* | 1/2003 | Menzies | A44B 18/0003 442/328 |
| 6,534,174 B1* | 3/2003 | Ouellette | B01D 39/163 428/292.1 |
| RE38,105 E | 5/2003 | James et al. | |
| 6,642,160 B1* | 11/2003 | Takahashi | A44B 18/0011 24/446 |
| RE38,505 E | 4/2004 | James et al. | |
| 6,735,833 B2 | 5/2004 | Putnam et al. | |
| 6,903,034 B1 | 6/2005 | Putnam et al. | |
| 7,091,140 B1 | 8/2006 | Ferencz et al. | |
| 7,406,755 B2 | 8/2008 | Putnam et al. | |
| 2001/0036787 A1 | 11/2001 | Brennan | B32B 5/26 442/361 |
| 2002/0019206 A1* | 2/2002 | Deka | A44B 18/0011 451/526 |
| 2003/0211801 A1* | 11/2003 | Putnam | D04H 1/495 442/387 |
| 2004/0137200 A1* | 7/2004 | Chhabra | D04H 1/54 428/167 |
| 2012/0156461 A1* | 6/2012 | Krishnamurthy | D04H 3/147 428/219 |
| 2015/0314560 A1* | 11/2015 | Kauschke | A47L 13/16 428/141 |
| 2016/0206393 A1* | 7/2016 | Wang | A61B 46/40 |

FOREIGN PATENT DOCUMENTS

| | | | |
|---|---|---|---|
| WO | 2003057960 A2 | 7/2003 | |
| WO | 2004079076 A1 | 9/2004 | |
| WO | WO-2007120629 A2 * | 10/2007 | ............. A47L 13/16 |

OTHER PUBLICATIONS

Second Written Opinion of the International Preliminary Examining Authority of corresponding International Application No. PCT/US2016/042476 dated Jun. 1, 2017, all enclosed pages cited.

Office action issued in Chilean patent application No. 00074-2018 dated Jul. 1, 2019, all enclosed pages cited.

English translation of Office action issued in Colombian patent application No. NC2018/0001250 dated Jul. 21, 2019, all enclosed pages cited.

Office Action (with English translation) issued in corresponding Japanese Patent Application No. 2018-501227 dated Aug. 25, 2020, all enclosed pages cited.

Office Action (with English translation) issued in corresponding Mexican Patent Application No. MX/a/2018/000378 dated Feb. 25, 2021, all enclosed pages cited.

\* cited by examiner

LOW LINTING IMAGED HYDROENTANGLED NONWOVEN COMPOSITE

PRIORITY CLAIM

This application claims priority under 35 U.S.C. §119(e) to U.S. Provisional Application Ser. No. 62/192,698, filed on Jul. 15, 2015, which is expressly incorporated by reference herein in its entirety.

TECHNICAL FIELD

The presently-disclosed invention relates generally to hydroentangled composites having various commercial applications.

BACKGROUND

Absorbent products, such as personal hygiene articles, require abrasion resistance and low linting in combination with good fluid handling characteristics (e.g., acquisition rate and rewet). Personal hygiene articles typically include a liner layer positioned between the wearer and an absorbent core. The purpose of this liner is to provide a surface suitable for contact with the skin and to contain the absorbent materials. The liners should be permeable to bodily fluids and allow rapid absorption by the core, thereby taking fluid away from the skin of the wearer at a high rate. Additionally, the liners should be thick enough to prevent migration of the liquid from the absorbent core back to the skin of the wearer when the wearer applies pressure to the product (e.g., when sitting). However, the liners typically used in personal hygienic articles are often a thin spunbond fabric. The low thickness of these spunbond fabrics makes it difficult to achieve good rewet properties without the use of a high performance acquisition and distribution layer that is typically placed between the liner and the absorbent core.

Therefore there at least remains a need in the art for three-dimensional composites that exhibit better separation, softness, low linting, low abrasion, bulk and good fluid handling characteristics (e.g., acquisition rate and rewet).

SUMMARY OF INVENTION

One or more embodiments of the invention may address one or more of the aforementioned problems. Certain embodiments according to the invention provide hydroentangled composites suitable for a wide variety of uses (e.g., personal hygiene articles, facers for fenestration absorbent patches on surgical drapes, facers on absorbent surgical drapes, etc.). In one aspect, the hydroentangled composite includes at least two nonwoven webs. The hydroentangled composite may comprise a three-dimensional pattern. Furthermore, the at least two nonwoven webs may have different bonding levels, for example, prior to being hydroentangled.

In accordance with certain embodiments of the invention, the at least two nonwoven webs may comprise a first nonwoven web and a second nonwoven web and at least one of the first nonwoven web and the second nonwoven web may comprise a spunbond. In certain embodiments of the invention, the first nonwoven web may have a first nonwoven web bonding level and the second nonwoven web may have a second nonwoven web bonding level. In such embodiments, the first nonwoven web bonding level may be lower than the second nonwoven web bonding level.

In accordance with certain embodiments of the invention, a first nonwoven web of the hydroentangled composite faces at least one water jet directed at the hydroentangled composite and a second nonwoven web of the hydroentangled composite faces an imaging sleeve and an amount of bonding energy of the second nonwoven web is at least about 5% greater than the bonding energy of the first nonwoven web.

In accordance with certain embodiments of the invention, the first nonwoven web may comprise a spunbond and the second nonwoven web may comprise a spunbond. In some embodiments of the invention, the spunbond may comprise at least one of a polyolefin, a polyester, or combinations thereof. In some embodiments of the invention, the spunbond may comprise at least one of a polypropylene, a polyethylene, a polyester, or combinations thereof. In other embodiments, the spunbond may comprise a polypropylene. In such embodiments of the invention, the spunbond may comprise an isotactic polypropylene. In certain embodiments of the invention, the first nonwoven web may comprise bicomponent fibers. Further pursuant to such embodiments of the invention, the bicomponent fibers may comprise a sheath comprising a polyethylene and a core comprising at least one of a polypropylene, a polyester, or a biopolymer (e.g., polylactic acid (PLA) polyhydroxyalkanoates (PHA), and poly(hydroxycarboxylic) acids). In further embodiments of the invention, the first nonwoven web may comprise bicomponent fibers and the second nonwoven web may comprise a polypropylene spunbond.

In accordance with certain embodiments of the invention, the hydroentangled composite may have a three-dimensional pattern. Further pursuant to these embodiments of the invention, the three-dimensional pattern may comprise substantially parallel ridges and depressions. In certain other embodiments of the invention, the three-dimensional pattern may comprise a zigzag pattern.

In accordance with certain embodiments of the invention, the hydroentangled composite may have a lint ratio between the second nonwoven web and the first nonwoven web from about 0.1 to about 0.9. In certain embodiments of the invention the hydroentangled composite may have a lint ratio between the second nonwoven web and the first nonwoven web from about 0.1 to about 0.75. In certain embodiments of the invention, the hydroentangled composite may have a lint ratio between the second nonwoven web and the first nonwoven web from about 0.15 to about 0.6. In other embodiments of the invention, the hydroentangled composite may have a lint ratio between the second nonwoven web and the first nonwoven web from about 0.2 to about 0.5. In certain embodiments of the invention, the hydroentangled composite may have a lint level from about 2 gsm to about 8 gsm. In yet other embodiments of the invention, the hydroentangled composite may have a lint level from about 2.5 gsm to about 6 gsm. In other embodiments, the hydroentangled composite may have a lint level from about 2.8 gsm to about 5 gsm. According to certain embodiments of the invention, the hydroentangled composite may be abrasion-resistant. In some embodiments of the invention, the hydroentangled composite may be absorbent.

In accordance with certain embodiments of the invention, the hydroentangled composite may have a basis weight from about 10 gsm to about 90 gsm. In certain embodiments of the invention, the hydroentangled composite may have a basis weight from about 20 gsm to about 60 gsm. In other embodiments of the invention, the hydroentangled composite may have a basis weight from about 30 gsm to about 50 gsm. According to certain embodiments of the invention, the hydroentangled composite may have a strength factor from about 1 N/gsm to about 2 N/gsm. In other embodiments of the invention, for example, the hydroentangled composite may have a strength factor from about 1.25 N/gsm to about 1.75 N/gsm. In yet other embodiments of the invention, for instance, the hydroentangled composite may have a strength factor from about 1.35 N/gsm to about 1.65 N/gsm.

In accordance with certain embodiments of the invention, the hydroentangled composite may comprise at least two nonwoven webs hydroentangled together, including a first nonwoven web and a second nonwoven web. In certain embodiments of the invention, the first nonwoven web has a first lint level prior to hydroentanglement defining a first bonding level and the second nonwoven web has a second lint level prior to hydroentanglement defining a second bonding level, in which the first lint level is greater than the second lint level. Hydroentangled composites according to certain embodiments of the invention may comprise a three-dimensional pattern, such as formed via a hydroentanglement process as disclosed herein. In certain embodiments of the invention, the second nonwoven web (the web having a lower lint level and/or higher bonding level prior to hydroentanglement) faces an imaging sleeve or surface and the first nonwoven web faces at least one water jet directed at the hydroentangled composite. Certain hydroentangled composite according to such embodiments, for example, may comprise a weighted linting level ratio between the two nonwoven webs (prior to being hydroentangled together) comprising a value less than about 0.9 (e.g., 0.3-0.9).

In another aspect, certain embodiments of the invention provide a process for forming a hydroentangled composite. The process includes providing a nonwoven material comprising at least two nonwoven webs having different bonding levels such that the at least two nonwoven webs include a first nonwoven web having a first nonwoven web bonding level and a second nonwoven web having a second nonwoven web bonding level, and applying at least one jet of fluid directly or indirectly to the first nonwoven web to impart a three-dimensional pattern onto the nonwoven material. Further pursuant to such embodiments of the invention, the first nonwoven web bonding level is lower than the second nonwoven web bonding level, the first nonwoven web is positioned facing at least one fluid jet and the second nonwoven web is positioned directly or indirectly onto an imaging surface or sleeve having a three-dimensional pattern. Suitable 3D imaging sleeves according to certain embodiments of the invention include those described, for example, in RE38,105 and RE38,505, in which the contents of both are hereby incorporated by reference in their entirety. In certain embodiments of the invention, the bonding level is a bonding energy and an amount of bonding energy of the second nonwoven web is at least about 5% greater than the bonding energy of the first nonwoven web.

According to certain embodiments of the invention, the process may further comprise pre-entangling the at least two nonwoven webs. Further pursuant to these embodiments of the invention, the at least two nonwoven webs may be pre-entangled via a hydroentangling process. According to certain embodiments of the invention, the process may further comprise applying a hydrophilic additive. In some embodiments of the invention, applying the hydrophilic additive may comprise melt dispersing the hydrophilic additive. In other embodiments of the invention, applying the hydrophilic additive may comprise topically applying the hydrophilic additive.

In accordance with certain embodiments of the invention, the at least two nonwoven webs may comprise a first nonwoven web and a second nonwoven web and at least one of the first nonwoven web and the second nonwoven web may comprise a spunbond. According to certain embodiments of the invention, the first nonwoven web may comprise a spunbond and the second nonwoven web may comprise a spunbond. In some embodiments of the invention, the spunbond may comprise at least one of a polyolefin, a polyester, a biopolymer (e.g., polylactic acid (PLA) polyhydroxyalkanoates (PHA), and poly(hydroxycarboxylic) acids, or combinations thereof. In yet other embodiments of the invention, the spunbond may comprise at least one of a polypropylene, a polyethylene, a polyester, or combinations thereof. In other embodiments, the spunbond may comprise a polypropylene. Further pursuant to such embodiments of the invention, the spunbond may comprise an isotactic polypropylene. In certain embodiments of the invention, the first nonwoven web may comprise bicomponent fibers. According to such embodiments of the invention, the bicomponent fibers may comprise a sheath comprising a polymer formulation that melt at a lower temperature than the polymer composition forming the core. According to such embodiments of the invention, the bicomponent fibers may comprise a sheath comprising polyethylene and a core comprising at least one of a polypropylene, a polyester, or a biopolymer (e.g., polylactic acid (PLA) polyhydroxyalkanoates (PHA), and poly(hydroxycarboxylic) acids). In further embodiments of the invention, the first nonwoven web may comprise bicomponent fibers and the second nonwoven web may comprise a polypropylene spunbond.

In accordance with certain embodiments of the invention, the hydroentangled composite may have a three-dimensional pattern. Further pursuant to such embodiments of the invention, the three-dimensional pattern may comprise substantially parallel ridges and depressions. In still other embodiments of the invention, the three-dimensional pattern may comprise a zigzag pattern.

In accordance with certain embodiments of the invention, the hydroentangled composite may have a lint ratio between the second nonwoven web and the first nonwoven web from about 0.1 to about 0.9. In certain embodiments, the hydroentangled composite may have a lint ratio between the second nonwoven web and the first nonwoven web from about 0.1 to about 0.75. In further embodiments of the invention, the hydroentangled composite may have a lint ratio between the second nonwoven web and the first nonwoven web from about 0.15 to about 0.6. In other embodiments of the invention, the hydroentangled composite may have a lint ratio between the second nonwoven web and the first nonwoven web from about 0.2 to about 0.5. In certain embodiments of the invention, the hydroentangled composite may have a lint level from about 2 gsm to about 8 gsm. In certain other embodiments of the invention, the hydroentangled composite may have a lint level from about 2.5 gsm to about 6 gsm. In other embodiments, the hydroentangled composite may have a lint level from about 2.8 gsm to about 5 gsm. According to certain embodiments of the invention, the hydroentangled composite may be abrasion-resistant. In some embodiments of the invention, the hydroentangled composite may be absorbent.

In accordance with certain embodiments of the invention, the hydroentangled composite may have a basis weight from about 10 gsm to about 90 gsm. According to certain embodiments of the invention, the hydroentangled composite may have a basis weight from about 15 gsm to about 60 gsm (e.g., 20-60 gsm). In other embodiments of the invention, the hydroentangled composite may have a basis weight from about 20 gsm to about 50 gsm (e.g., 30-50 gsm). According to certain embodiments of the invention, the hydroentangled composite may have a strength factor from about 1 N/gsm to about 2 N/gsm. In certain other embodiments of the invention, for example, the hydroentangled composite may have a strength factor from about 1.25 N/gsm to about 1.75 N/gsm. In other embodiments of the invention, for instance, the hydroentangled composite may have a strength factor from about 1.35 N/gsm to about 1.65 N/gsm.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 6:
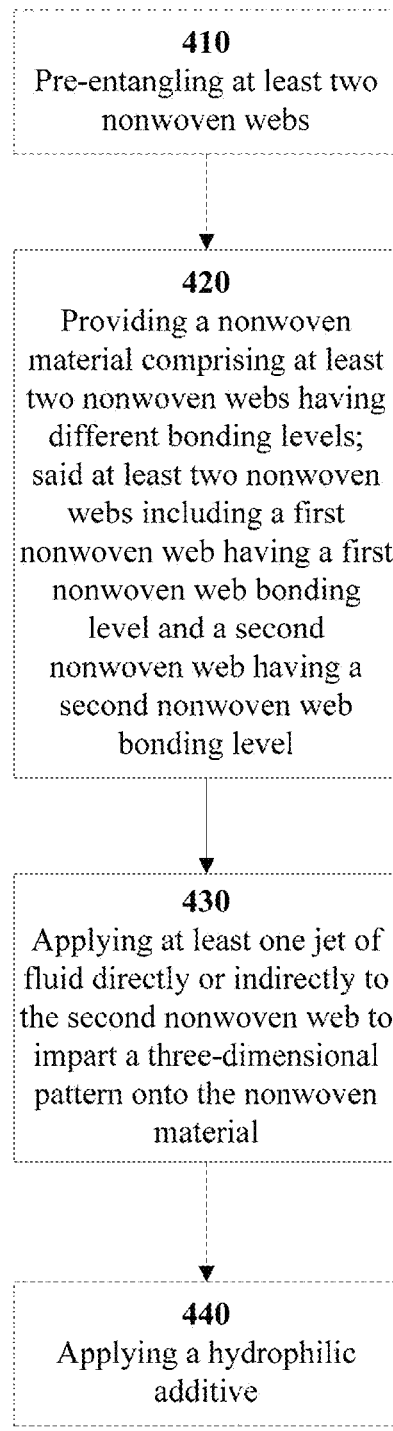
Figure 7A:
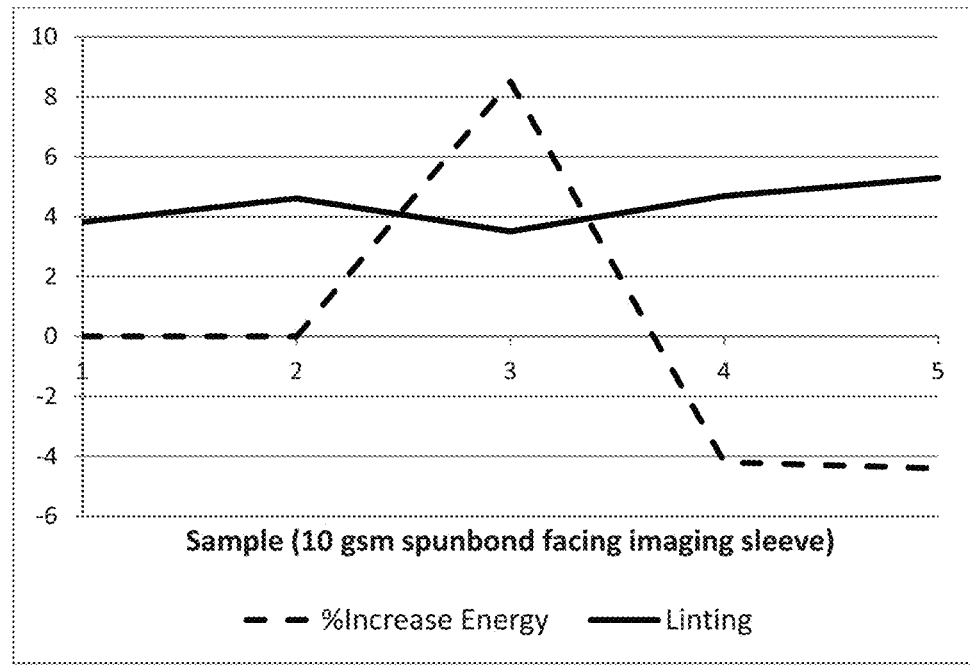
Figure 7B:
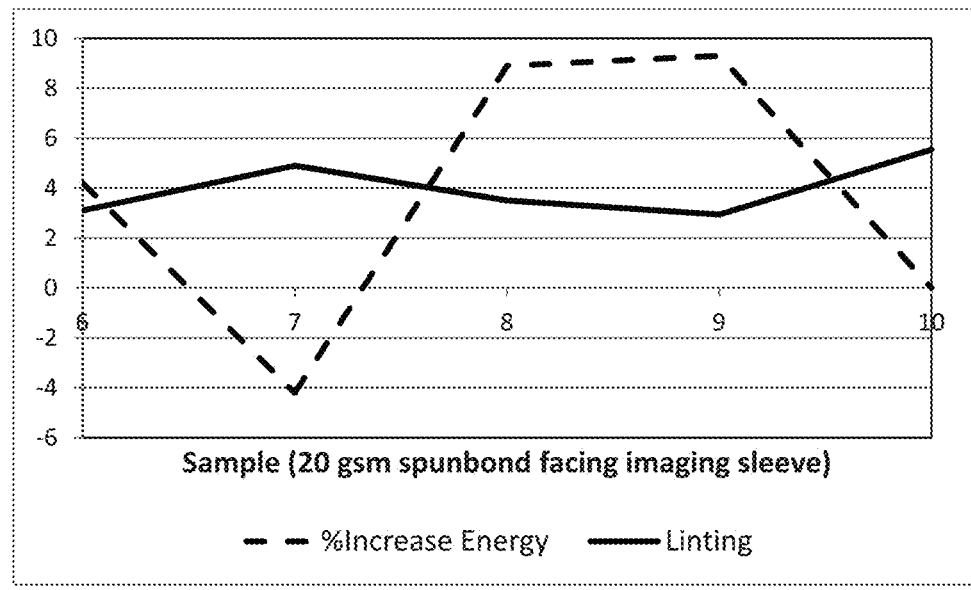

FIG. 6 illustrates a process flow diagram for forming a hydroentangled composite according to an embodiment of the invention showing optional steps of pre-entangling at least two nonwoven webs and applying a hydrophilic additive to the hydroentangled composite; and FIGS. 7A and 7B show the percentage increase in bonding energy between the spunbond facing the imaging sleeve and the spunbond facing the water jets plotted against the linting for the composite for the spunbond facing the water jet having a basis weight of 10 gsm and 20 gsm, respectively

DETAILED DESCRIPTION

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The invention includes, according to certain embodiments, a hydroentangled composite based, at least in part, on at least two nonwoven webs, such that the hydroentangled composite has a three-dimensional pattern, and the at least two nonwoven webs have different bonding levels and/or linting levels. Hydroentangled composites, according to certain embodiments of the invention, may exhibit better separation, softness, low linting, and good fluid handling characteristics (e.g., acquisition rate and rewet).

The terms "substantial" or "substantially" may encompass the whole amount as specified, according to certain embodiments of the invention, or largely but not the whole amount specified according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantiomers; and/or any chiral molecular configuration of such polymer or polymeric material. These configurations include, but are not limited to, isotactic, syndiotactic, and atactic configurations of such polymer or polymeric material. The term "polymer" or "polymeric" shall also include polymers made from various catalyst systems including, without limitation, the Ziegler-Natta catalyst system and the metallocene/single-site catalyst system. The term "polymer" or "polymeric" shall also include polymers produced by fermentation process or biosourced.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, hydroentangling, air-laid, and bonded carded web processes.

The term "layer", as used herein, may comprise a generally recognizable combination of similar material types and/or functions existing in the X-Y plane.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous. It is noted that the spunbond used in certain composites of the invention may include a nonwoven described in the literature as SPIN-LACE®.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers are microfibers which may be continuous or discontinuous and are generally tacky when deposited onto a collecting surface.

The term "hydroentangle" or "hydroentangled", as used herein, may comprise a process for bonding a nonwoven fabric by using high pressure water jets to intermingle the fibers. Several rows of water jets are directed against the fiber web, which is supported by a movable fabric. Fiber entanglements are introduced by the combined effects of the water jets and the turbulent water created in the web, which intertwines neighboring fibers.

The term "laminate", as used herein, may be a structure comprising two or more layers, such as a film layer and a fibrous layer. The two layers of a laminate structure may be joined together such that a substantial portion of their common X-Y plane interface, according to certain embodiments of the invention.

As used herein, the terms "consolidation" and "consolidated" may comprise the bringing together of at least a portion of the fibers of a nonwoven web into closer proximity or attachment there-between (e.g., fused together) to form a bonding site, or bonding sites, which function to increase the resistance of the nonwoven to external forces (e.g., abrasion and tensile forces), as compared to the unconsolidated web. The bonding site or bonding sites, for example, may comprise a discrete or localized region of the web material that has been softened or melted and optionally subsequently or simultaneously compressed to form a discrete or localized deformation in the web material. Furthermore, the term "consolidated" may comprise an entire nonwoven web that has been processed such that at least a portion of the fibers are brought into closer proximity or attachment there-between (e.g., fused together), such as by thermal bonding as merely one example. Such a web may be considered a "consolidated nonwoven" according to certain embodiments of the invention. Additionally, a specific, discrete region of fibers that is brought into close proximity or attachment there-between (e.g., fused together), such as an individual bond site, can be described as "consolidated".

The term "Weighted Linting Level" (WLL) is defined as the linting result (L) for a web multiplied by its basis weight (BWt). For example a web having a basis weight of 10.3 gsm and a lint level of 0.18 gsm will have a WLL of 1.85. WLL may be calculated according to the following formula:

$$WLL = (L * BWt).$$

The term "Strength factor" is also defined as SF is the sum of the strip tensile strengths of a web or composite in the machine (S1) and the cross direction (S2) divided by the basis weight (BW) of the web or composite. SF may be calculated according to the following formula:

$$SF = (S1 + S2)/BW.$$

Figure 1:
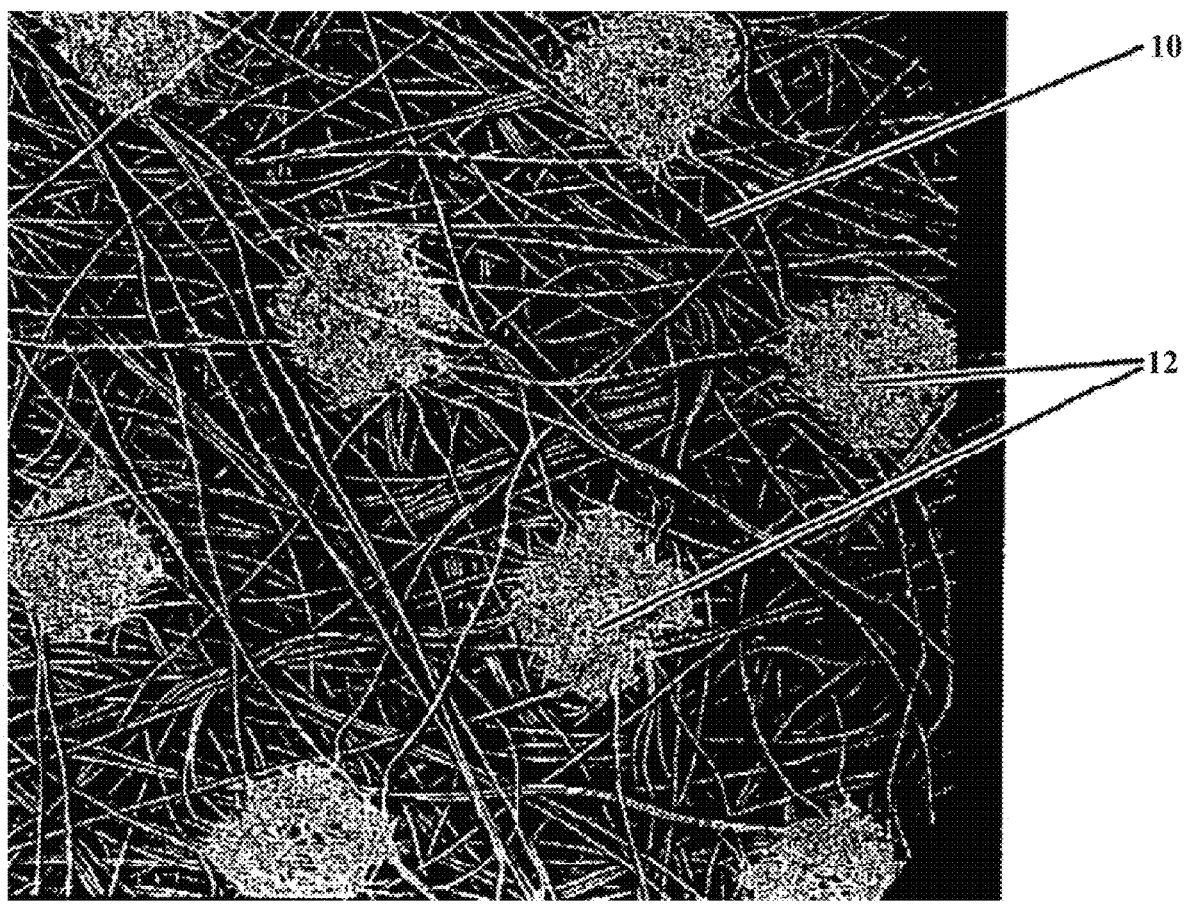
FIG. 1 is a micrograph illustrative of a consolidated nonwoven web having a plurality of discrete thermal bond sites.

In accordance with certain embodiments of the invention, consolidation may be achieved by methods that apply, for example, heat and/or pressure to the fibrous web. One non-limiting and exemplary method comprises thermal bonding (e.g., thermal point bonding). Thermal point bonding can be accomplished by passing the fibrous web through a pressure nip formed by two rolls, one of which is heated and contains a plurality of raised protrusions having one or more geometric shapes (e.g., points, diamond shaped, circular, elliptical, dog-bone shaped, etc.) on its surface which impart or form corresponding discrete thermal bond sites on the fibrous web. Additional non-limiting and exemplary consolidation methods according to certain embodiments of the invention can also include ultrasonic bonding, through-air bonding, and hydroentanglement. The degree or extent of consolidation may be expressed as a percentage of the total surface area of the web that has been consolidated or subjected to consolidation and referred to as a "bonding are" or "consolidation area". Stated somewhat differently, the terms "bonding area" and "consolidated area", as used interchangeably herein, may comprise the area per unit area occupied by the localized sites formed by bonding the fibers into bond sites an may be expressed as a percentage of total unit area of the consolidated nonwoven. For example, consolidated nonwovens may comprise a plurality of discrete, spaced-apart bond sites formed by bonding only the fibers of the nonwoven in the area of localized energy input. Fibers or portions of fibers remote from the localized energy input remain substantially unbonded to adjacent fibers. In this regard, the consolidated nonwoven may also be referred to as partially consolidated since the entire surface of the web has not been consolidated. By way of example only, FIG. 1 shows a consolidated nonwoven 10 comprising a plurality of discrete thermal bond sites 12. Although the particular consolidated nonwoven 10 shown in FIG. 1 has a consolidation area of about 14% with a pattern of regularly spaced apart diamond-shaped bond sites (e.g., each diamond-shaped bond site has a long dimension of about 0.9 mm and a short dimension of about 0.8 mm), the general pattern shown in FIG. 1 may be readily modified by one of ordinary skill in the art. For example, the size, number, shape and relative positioning of the individual bond sites 12 may be varied as desired.

The term "bicomponent fibers", as used herein, may comprise fibers formed from at least two different polymers extruded from separate extruders but spun together to form one fiber. Bicomponent fibers are also sometimes referred to as conjugate fibers or multicomponent fibers. The polymers are arranged in a substantially constant position in distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement, each as is known in the art of multicomponent, including bicomponent, fibers. The "bicomponent fibers" may be thermoplastic fibers that comprise a core fiber made from one polymer that is encased within a thermoplastic sheath made from a different polymer or have a side-by-side arrangement of different thermoplastic fibers. The first polymer often melts at a different, typically lower, temperature than the second polymer. In the sheath/core arrangement, these bicomponent fibers provide thermal bonding due to melting of the sheath polymer, while retaining the desirable strength characteristics of the core polymer. In the side-by-side arrangement, the fibers shrink and crimp creating z-direction expansion.

The terms "lint" and "lint level", as used herein, may comprise the tendency of a web to shed particles when manipulated. This tendency may be measured in accordance to the standard test method WSP 400.0 (05) with the modifications as described in the Example section.

I. Hydroentangled Composite

In one aspect, the invention provides hydroentangled composites suitable for a wide variety of uses (e.g., personal hygiene articles, facers for fenestration absorbent patches on surgical drapes, facers on absorbent surgical drapes, etc.). Hydroentangled composites, according to certain embodiments of the invention, may include at least two nonwoven webs. The hydroentangled composite may comprise a three-dimensional pattern. Furthermore, the at least two nonwoven webs, which are hydroentangled together, may have different bonding levels and/or different lint levels. In accordance with certain embodiments of the invention, the side of the hydroentangled composite defined or associated with the nonwoven web having the higher web bonding level and/or lower lint level prior to being hydroentangled together may define a contact side of the hydroentangled composite which may be exposed to a wearer's skin. According to certain embodiments of the invention, the at least two nonwoven webs may comprise substantially the same or different consolidation areas as discussed below.

In accordance with certain embodiments of the invention, for instance, the at least two nonwoven webs may comprise a first nonwoven web and a second nonwoven web. In certain embodiments of the invention, for example, the first nonwoven web may have (i) a first nonwoven web bonding level and (ii) a first consolidation area; and the second nonwoven web may have (i) a second nonwoven web bonding level and (ii) a second consolidation area. Further pursuant to such embodiments of the invention, for instance, the first nonwoven web bonding level may be lower than the second nonwoven web bonding level prior to being hydroentangled together. The at least two nonwoven webs, including the first nonwoven web and the second nonwoven web, may each comprise substantially the same or different consolidation areas, in which the respective consolidation area for each nonwoven web may be selected independent from the web bonding level of each nonwoven web. In certain embodiments of the invention, for example, the first nonwoven web bonding level may be lower than the second nonwoven web bonding level while the first web consolidation area may be greater than the second nonwoven consolidation area. In additional embodiments of the invention, for example, the first nonwoven web bonding level may be lower than second nonwoven bonding level while the first web consolidation area may also be lower than the second nonwoven consolidation area. In accordance with certain embodiments of the invention, the at least two nonwoven webs may comprise substantially the same consolidation area (e.g., all nonwoven webs have a consolidation area within 10%, 5%, or 3% of each other). In accordance with certain embodiments of the invention, for instance, the each of the bonding level and the consolidation area for each and every nonwoven web may be selected independently.

In accordance with certain embodiments of the invention, the hydroentangled composite may comprise at least two nonwoven webs hydroentangled together, including a first nonwoven web and a second nonwoven web. In certain embodiments of the invention, the first nonwoven web has a first lint level prior to hydroentanglement defining a first bonding level and the second nonwoven web has a second lint level prior to hydroentanglement defining a second bonding level, in which the first lint level is greater than the second lint level. Hydroentangled composites according to certain embodiments of the invention may comprise a three-dimensional pattern, such as formed via a hydroentanglement process as disclosed herein. In certain embodiments of the invention, the second nonwoven web (the web having a lower lint level and/or higher bonding level prior to hydroentanglement) faces an imaging sleeve or surface and the first nonwoven web faces at least one water jet directed at the hydroentangled composite. Certain hydroentangled composite according to such embodiments, for example, may comprise a weighted linting level ratio between the second nonwoven web and the first nonwoven web (prior to being hydroentangled together) comprising a value less than about 0.9 (e.g., 0.3-0.9).

The at least two nonwoven webs, in accordance with certain embodiments of the invention, may each independently from all other nonwoven webs have consolidation area from at least about any of the following: 3, 5, 7, 10, 12, 14, and 15% and/or at most about 50, 45, 40, 30, 25 and 20%. By way of example only, the at least two nonwoven webs may include the first nonwoven web having the first nonwoven web consolidation area from between 3 and 12% and the second nonwoven web having the second nonwoven web consolidation area from between 15 and 30%. In such an exemplary embodiment, the first nonwoven bonding level may comprise a value greater than the second nonwoven bonding level.

In certain embodiments of the invention, the at least two nonwoven webs may comprise substantially the same or different bonding pattern. For instance, the size, number, shape, and relative positioning of individual bond sites forming the bonding patterns may be independently varied as desired. In certain embodiments of the invention, for example, the at least two nonwoven webs may comprise the first nonwoven web having a plurality of discrete and localized diamond-shaped bonding sites while the second nonwoven web may have a plurality of discrete and localized elliptical-shaped bonding sites. Additionally or alternatively to any of the foregoing embodiments of the invention, the first nonwoven may comprise a first nonwoven bonding pattern and the second nonwoven may comprise a second nonwoven bonding pattern, in which the first nonwoven bonding pattern (e.g., random pattern) is different than the second nonwoven bonding pattern (e.g., regular and repeating pattern).

As noted above, the bonding pattern of the at least two nonwoven webs may comprise substantially the same or different types of bonding sites (e.g., bonding sites formed by various consolidation methods). In accordance with certain embodiments of the invention, for example, each nonwoven of the at least two nonwovens may be subjected to the same or different consolidation method. The bonding sites on each nonwoven web, for example, may be formed from one or more of a variety of consolidation methods such as calendaring (e.g., thermal point bonding) or ultrasonic bonding. In certain embodiments of the invention, for example, the first nonwoven may comprise a plurality of discrete or localized bonding sites comprising thermal point bonds while the second nonwoven may comprise a plurality of discrete or localized bonding sites formed by an ultrasonic bonding technique.

In accordance with certain embodiments of the invention, for example, at least one of the first nonwoven web and the second nonwoven web may comprise a spunbond. In certain embodiments of the invention, for instance, the first nonwoven web may comprise a spunbond and the second nonwoven web may comprise a spunbond. In some embodiments of the invention, for example, the spunbond may comprise at least one of a polyolefin, a polyester, or combinations thereof. In other embodiments of the invention, for instance, the spunbond may comprise at least one of a polypropylene, polyethylene, polyester, or combinations thereof. In other embodiments, for example, the spunbond may comprise a polypropylene. Further pursuant to such embodiments of the invention, for instance, the spunbond may comprise an isotactic polypropylene. In certain embodiments of the invention, for example, the spunbond may comprise a polyethylene. In such embodiments of the invention, for instance, the spunbond may comprise high density polyethylene ("HDPE"), low density polyethylene ("LDPE"), linear low density polyethylene ("LLDPE"), a copolymer of ethylene and any combination thereof.

According to certain embodiments of the invention, for example, the first nonwoven web may comprise bicomponent fibers. Further pursuant to such embodiments of the invention, for instance, the bicomponent fibers may comprise a sheath comprising polyethylene and a core comprising at least one of a polypropylene or a polyester. In further embodiments of the invention, for example, the first nonwoven web may comprise bicomponent fibers and the second nonwoven web may comprise a polypropylene spunbond.

According to certain embodiments of the invention, for example, the hydroentangled composite may comprise more than two nonwoven webs. Exemplary configurations include, but are not limited to, $S_1S_1S_2$, $S_1S_1S_2S_2$, and $S_1S_2S_2$, where $S_1$=the first nonwoven web and $S_2$=the second nonwoven web. In further embodiments, for instance, at least one of the first nonwoven web or the second nonwoven web may comprise an SMS configuration, where S=spunbond and M=meltblown. In other embodiments of the invention, for example, at least one of the first nonwoven web or the second nonwoven web may comprise a laminate. Further pursuant to such embodiments of the invention, for instance, the laminate may comprise a meltblown layer captured between two layers of continuous filaments or multiple layers of continuous filaments (e.g., spunbond).

In accordance with certain embodiments of the invention, for example, the hydroentangled composite may be abrasion-resistant. In some embodiments, for instance, the hydroentangled composite of the invention may be absorbent. According to certain embodiments, for example, the hydroentangled composite of the invention may have low linting. In such embodiments, for instance, the hydroentangled composite of the invention may have a lint level from about 2 gsm to about 8 gsm. In further embodiments, for example, the hydroentangled composite of the invention may have a lint level from about 2.5 gsm to about 6 gsm. In other embodiments, for instance, the hydroentangled composite of the invention may have a lint level from about 2.8 gsm to about 5 gsm. As such, in certain embodiments, the hydroentangled composite of the invention may have a lint level from at least about any of the following: 2, 2.25, 2.5, 2.75, and 2.8 gsm and/or at most about 8, 7, 6, 5.5, and 5 gsm (e.g., about 2.25-6 gsm, about 2-5 gsm, etc.).

According to certain embodiments of the invention, for instance, the hydroentangled composite may have a lint ratio between the second nonwoven web and the first nonwoven web from about 0.1 to about 0.9. In certain embodiments of the invention, the hydroentangled composite may have a lint ratio between the second nonwoven web and the first nonwoven web from about 0.1 to about 0.75. In further embodiments, for example, the hydroentangled composite of the invention may have a lint ratio between the second nonwoven web and the first nonwoven web from about 0.15 to about 0.6. In other embodiments, for instance, the hydroentangled composite of the invention may have a lint ratio between the second nonwoven web and the first nonwoven web from about 0.2 to about 0.5. As such, in certain embodiments, the hydroentangled composite of the invention may have a lint ratio between the second nonwoven web and the first nonwoven web from at least about any of the following: 0.1, 0.12, 0.15, 0.18, and 0.2 and/or at most about 0.9, 0.85, 0.8, 0.75, 0.7, 0.6, 0.55 and 0.5 (e.g., about 0.12-0.55, about 0.1-0.5, etc.).

In accordance with certain embodiments of the invention, for example, the hydroentangled composite may comprise a weighted lint ratio between the second nonwoven web and the first nonwoven web prior to being hydroentangled together comprises less than about 0.9, less than about 0.8, or less than about 0.7. In certain embodiments of the invention, for instance, the hydroentangled composite may comprise a weighted lint ratio between the second nonwoven web and the first nonwoven web prior to being hydroentangled together comprising from at least about any of the following: 0.1, 0.15. 0.2, 0.25, 0.3, 0.35, and 0.4 and/or at most about 0.95, 0.9, 0.85, 0.8, 0.75, 0.7, 0.65, 0.6, 0.55, 0.5, and 0.45 (e.g., about 0.3-0.9, about 0.4-0.9, etc.)

In accordance with certain embodiments of the invention, for example, the hydroentangled composite may have a basis weight from about 10 gsm to about 90 gsm. In further embodiments, for instance, the hydroentangled composite of the invention may have a basis weight from about 20 gsm to about 60 gsm. In other embodiments, for example, the hydroentangled composite of the invention may have a basis weight from about 30 gsm to about 50 gsm. As such, in certain embodiments, the hydroentangled composite of the invention may have a basis weight from at least about any of the following: 10, 15, 20, 25, and 30 gsm and/or at most about 90, 80, 70, 60, and 50 gsm (e.g., about 15-60 gsm, about 20-50 gsm, about 20-80 gsm, about 10-90 gsm, etc.).

In accordance with certain embodiments of the invention, for instance, the hydroentangled composite may have a strength factor from about 1 N/gsm to about 2 N/gsm. In further embodiments, for example, the hydroentangled composite of the invention may have a strength factor from about 1.25 N/gsm to about 1.75 N/gsm. In other embodiments, for instance, the hydroentangled composite of the invention may have a strength factor from about 1.35 N/gsm to about 1.65 N/gsm. As such, in certain embodiments, the hydroentangled composite of the invention may have a strength factor from at least about any of the following: 1, 1.25, 1.35, 1.4, and 1.5 N/gsm and/or at most about 2, 1.9, 1.8, 1.75, and 1.65 N/gsm (e.g., about 1.35-1.9 N/gsm, about 1.5-2 N/gsm, etc.).

In accordance with certain embodiments of the invention, for example, the hydroentangled composite may have a three-dimensional pattern. Further pursuant to such embodiments of the invention, for instance, the three-dimensional pattern may comprise substantially parallel ridges and depressions. In further embodiments of the invention, for example, the three-dimensional pattern may comprise a zigzag pattern.

Figure 2:
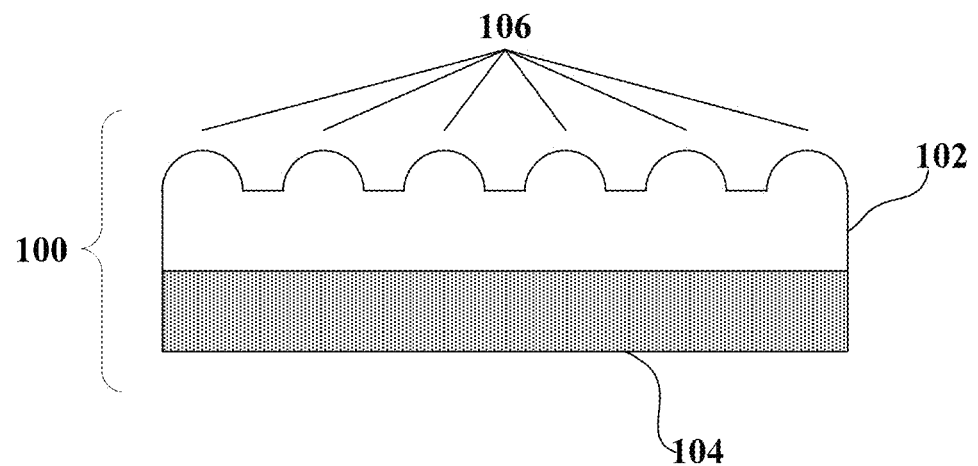
FIG. 2 illustrates a cross sectional view of a hydroentangled composite according to an embodiment of the invention.

For example, FIG. 2 illustrates a cross sectional view of a hydroentangled composite according to an embodiment of the invention. As shown in FIG. 2, the hydroentangled composite 100 includes a first nonwoven web 102 and a second nonwoven web 104, which have been hydroentangled together. The hydroentangled composite 100 also includes a three-dimensional pattern 106 on a surface of the first nonwoven web 102. Although the cross section view illustrated in FIG. 2 indicates that the imaging (e.g., three-dimensional pattern 106) affects only the first nonwoven web 102, this should not considered to be limiting, since the imaging process may also affect both the first and second nonwoven webs according to certain embodiments of the invention. Further pursuant to these embodiments of the invention, the second nonwoven web may include a three-dimensional pattern.

Figure 3:
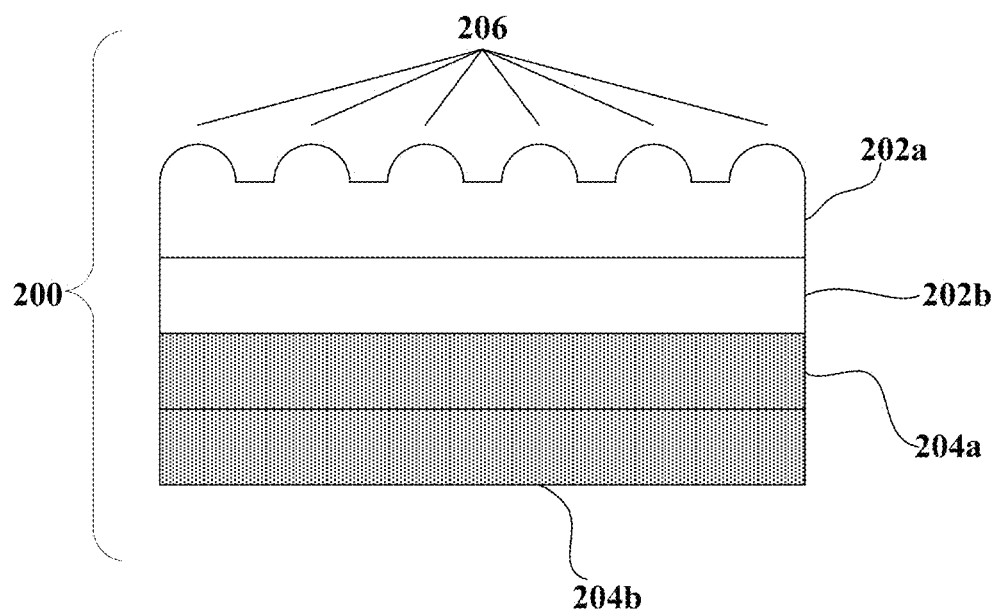
FIG. 3 illustrates a cross sectional view of a hydroentangled composite according to an embodiment of the invention.

FIG. 3, for example, illustrates a cross sectional view of a hydroentangled composite according to an embodiment of the invention. As shown in FIG. 3, the hydroentangled composite 200 includes a first layer of the first nonwoven web 202a, a second layer of the first nonwoven web 202b, a first layer of the second nonwoven web 204a, and a second layer of the second nonwoven web 204b. The hydroentangled composite 200 also includes a three-dimensional pattern 206 on a surface of the first layer of the first nonwoven web 202a. Although the cross section view illustrated in FIG. 3 indicates that the imaging (e.g., three-dimensional pattern 206) affects only the first layer of the first nonwoven web 202a, the imaging process may affect all layers 202a, 202b, 204a, 204b of the composite. For instance, each of the layers 202a, 202b, 204a, 204b of the composite may also include a three-dimensional pattern.

Figure 4:
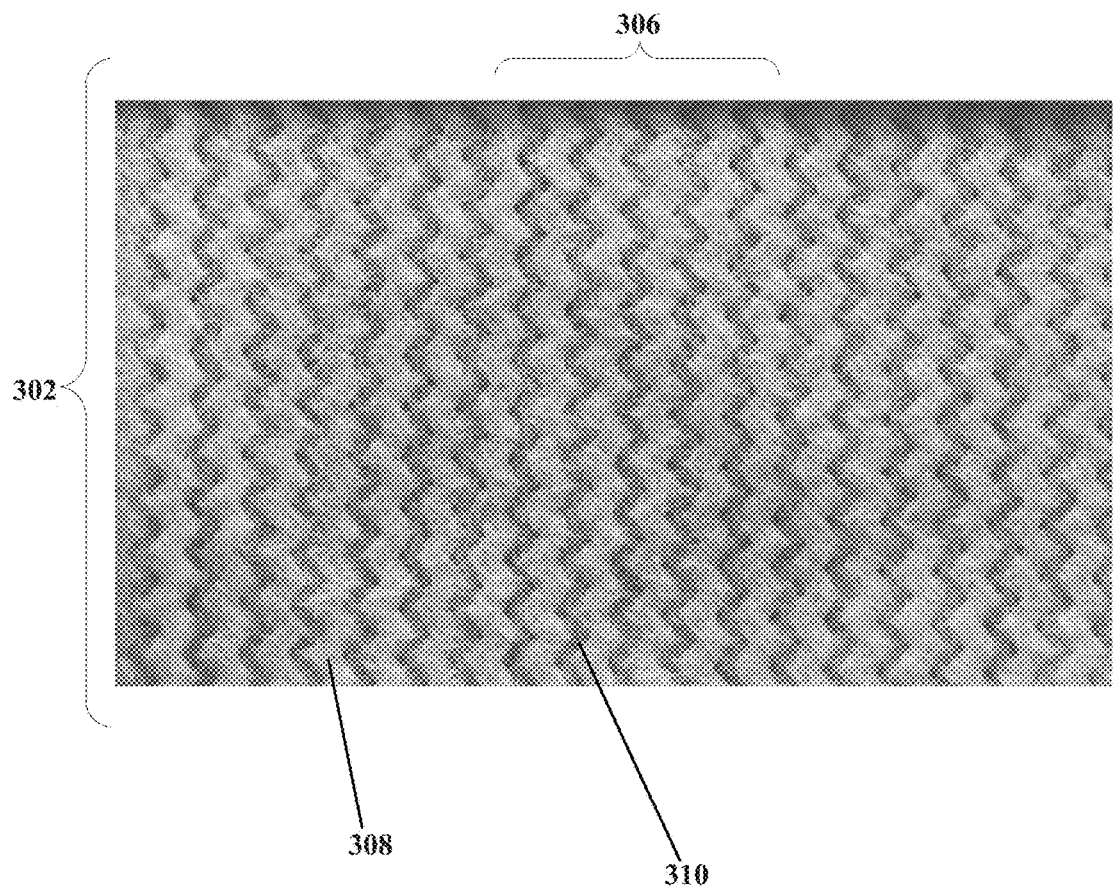
FIG. 4 illustrates a top plan view of a hydroentangled composite having a zigzag pattern according to an embodiment of the invention.

FIG. 4, for example, illustrates a top plan view of a hydroentangled composite having a zigzag pattern according to an embodiment of the invention. As shown in FIG. 4, the first nonwoven web 302 has a three-dimensional pattern 306 (e.g., zigzag pattern) on one surface. The three-dimensional pattern 306, for example, includes substantially parallel ridges 308 and depressions 310.

II. Bonding Level

The inventors have discovered that the extent of varying bonding between two or more nonwovens of a hydroentangled composite of the invention can control the extent of linting within the composite. Any of the nonwovens webs of the hydroentangled composite of the invention may comprise a spunbond web or a meltblown web. Indeed, as further disclosed herein, in certain embodiments, the hydroentangled composited of the invention may comprise any combination of spunbond and/or meltblown layers.

Generally, most nonwoven webs have inferior strength in the non-bonded form. The individual fibers or filaments that make up the nonwoven web must be interconnected or tied together in some form typically through gluing, thermally bonding, mechanical entanglement, and any combination of these techniques. The extent the individual fibers or filaments become interconnected or tied together in the web may control the extent of bonding within the web according to various embodiments of the invention.

Nonwoven webs used in the hydroentangled composite of the invention may become bonded by any technique known in the art. Exemplary, but non-limiting, techniques that may be used to bond the nonwoven webs include thermal bonding, latex bonding, thermal bonding, solvent bonding, mechanical bonding, ultrasonic bonding, needlepunching, spunlacing, stitchbonding, and any combination thereof.

Thermal bonding comprises fusing fiber surfaces to one another throughout the nonwoven web. For example, a non-limiting technique for thermal bonding nonwoven webs involves fusing the fibers by softening the fiber surface. Alternative embodiments comprise including and then melting fusible additives in the form of fibers, powders or particulates throughout the nonwoven web. Non-limiting examples of thermal bonding techniques include calendaring and through-air heating.

Figures 5A, 5B:
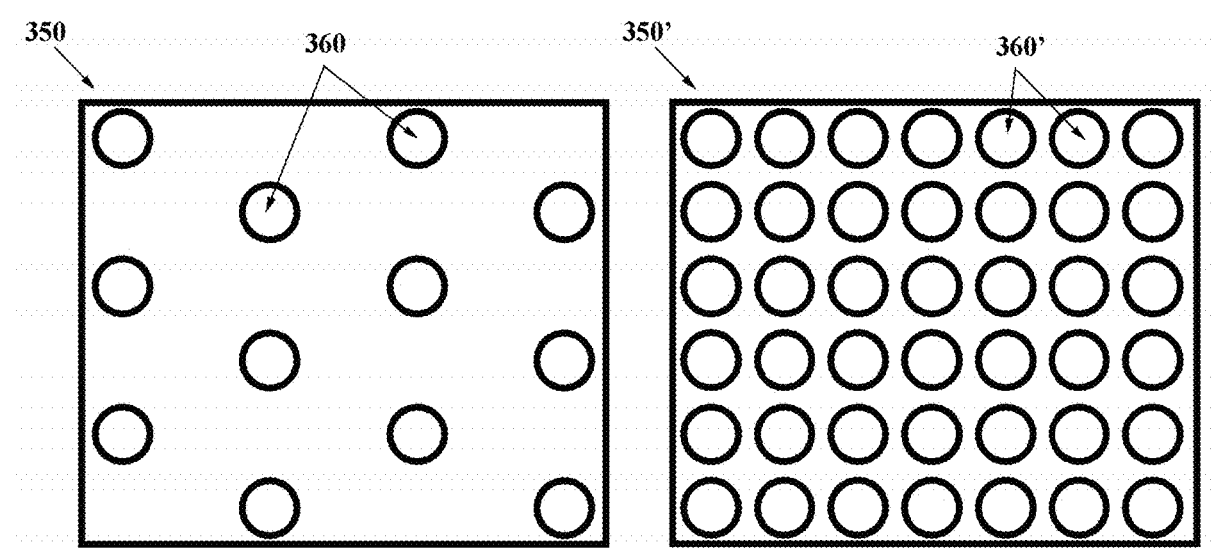
FIGS. 5A and 5B illustrate the extent of point bonding within exemplary but non-limiting embodiments of a nonwoven web that may be useful in certain embodiments of the invention.

Calendering involves drawing the nonwoven web between heated cylinders that have an embossed pattern allowing only part of the web to become exposed to heat and pressure supplied by the cylinder. The extent of embossing may be determinative of the extent or level of bonding of the nonwoven web. FIG. 5A illustrates the extent of point bonding 360 within an exemplary but non-limiting embodiment of a nonwoven web 350 that may be useful in certain embodiments of the invention. In contrast FIG. 5B illustrates the extent of point bonding 360' within another exemplary but non-limiting embodiment of a nonwoven web 350' that may be useful in certain embodiments of the invention. The point bonded, nonwoven web 350 of FIG. 5A would be representative of a nonwoven web having a lower bonding level relative to the nonwoven web 350' of FIG. 5B since the overall area bonded in the nonwoven web 350 of FIG. 5A is lower than the overall area bonded in the nonwoven web 350' of FIG. 5B. The extent of bonded area in the nonwoven web 350' of FIG. 5B is about 250% greater than the extent of bonded area in the nonwoven web 350 of FIG. 5A. According to certain embodiments of the invention, the extent of bonded area in the nonwoven web having a greater extent of bonding level is at least about 2%, at least about 4%, at least about 5%, at least about 8%, at least about 10%, at least about 15%, at least about 20%, at least about 25%, at least about 30%, at least about 40%, at least about 50%, at least about 75%, at least about 90%, at least about 100%, at least about 150%, at least about 200%, at least about 250%, at least about 300%, at least about 400%, or at least about 500% greater than the bonded area in the nonwoven web having a lesser extent of bonding level.

Of course there are other types of bonding images other than the point bonding images shown in FIGS. 5A and 5B. In addition to point bonding, nonwoven webs may be area bonded, according to certain embodiments of the invention. In area bonding, bonds are produced throughout the entire nonwoven fabric at locations where the fibers of the nonwoven fabric come into contact with one another. This can be achieved in various ways, such as by passing heated air, steam or other gas through a non-bonded web of fibers to cause the fibers to melt and fuse to one another at points of contact. The extent of thermal energy supplied to the nonwoven web by use of heated air, steam, or other gas will largely determine the extent of bonding within the nonwoven web. According to certain embodiments of the invention, the amount of thermal energy applied to the nonwoven web having a greater extent of bonding level is at least about 1%, at least about 2%, at least about 3%, at least about 4%, at least about 5%, at least about 6%, at least about 7%, at least about 8%, at least about 9%, at least about 10%, at least about 12%, at least about 15%, at least about 20%, at least about 25%, at least about 30%, at least about 35%, at least about 40%, at least about 45%, at least about 50%, or at least about 75% greater than the thermal energy applied to the nonwoven web having a lesser extent of bonding level.

According to an embodiment of the invention, the hydroentangled composite comprises at least two spunbond layers, where one of these spunbond layers faces water jets and another of these spunbond layers faces an imaging sleeve, the water jets and the imaging sleeve are used to impart an image to the hydroentangled composite. Suitable 3D imaging sleeves according to certain embodiments of the invention include those described, for example, in RE38,105 and RE38,505, in which the contents of both are hereby incorporated by reference in their entirety. Further pursuant to this embodiment of the invention, the amount of bonding energy to form the spunbond that faces the 3D imaging sleeve or surface is greater than at least about 1%, at least about 2%, at least about 3%, at least about 4%, at least about 5%, at least about 6%, at least about 7%, at least about 8%, at least about 9%, at least about 10%, at least about 12%, at least about 15%, at least about 20%, at least about 25%, at least about 30%, at least about 35%, at least about 40%, at least about 45%, at least about 50%, or at least about 75% in comparison to the amount of bonding energy to form the spunbond facing the waterjet(s).

Thermal bonding fibers, powders and particulates may comprise fusible polymers such as a polyethylene, a polypropylene, and a polyester. Typically, for calendaring, the binder fibers are often monocomponent. The fusing process destroys the original shape of the fibers, powders or particulates, but retains the structure in the non-bonded regions.

In embodiments where fibers of the nonwoven web comprise bicomponent fibers, a lower melting point polymer typically is disposed at or along, at least in part, the outside surface of the bicomponent fiber. During fusion and subsequent bonding, the low melting point polymer softens and flows to form the bond while the high melting point component substantially maintains its fiber shape and structural integrity. As a person of ordinary skill in the art would comprehend having the benefit of this disclosure, both the amount of low melting point component in the fiber of the nonwoven web and the extent of energy (e.g., heat) supplied to the nonwoven web will be determinative of the extent of bonding in the nonwoven web relative to other webs bonded in the same manner but having perhaps a different amount of low melting point component in the fiber of the nonwoven web and/or the extent of energy (e.g., heat) supplied to the nonwoven web.

Through-air thermal bonding uses hot air to fuse the fibers at the surface of the web as well as internally within the web. Hot air can either be blown through the web in a conveyorized oven or sucked through the web as it passes over a porous drum as a vacuum is developed. The temperature of and the rate of hot air are parameters that may determine the level or the extent of bonding in nonwoven web. In the case when fusible additives are included in the nonwoven web, the properties of the additive itself and the strength of the bond between the additive and the fibers of the nonwoven web may determine the bonding level within the nonwoven web.

Latex bonding involves the use of an adhesive resin or a binder that is applied to the web typically by any one of dipping the web into the binder, for example, through full or partial saturation bonding, and removing any excess or disposing the binder onto and/or throughout the web by spraying, foaming, and/or printing techniques. Gravure printing and screen printing are non-limiting examples of printing techniques for disposing a binder onto a nonwoven web. In certain embodiments, the extent of bonding level in a nonwoven web of the hydroentangled composite of the invention that are bonded through latex or resin bonding may be controlled by the amount of binder used in forming the web or even the extent of coverage the binder on the web. In an exemplary embodiment of the invention, the amount of binder in a nonwoven having a lesser extent of bonding may comprise from about 5 wt % to about 35 wt %, preferably from about 10 wt % to about 30 wt %, based upon the total weight of the nonwoven having a lesser extent of bonding while the amount of binder in a nonwoven having a greater extent of bonding may comprise from about 15 wt % to about 50 wt %, preferably from 20 wt % to about 40 wt % based upon the total weight of the nonwoven having a greater extent of bonding.

According to certain embodiments of the invention, the types of binders in the nonwovens may be different to impart different extensibility of bonding between the nonwoven webs. Without intending to be bound by theory, weaker binders tend to exhibit a lesser degree of adhesion between the fibers of the nonwoven web, while stronger binders tend to exhibit a greater degree of adhesion between the fibers of the nonwoven web. Water-based phenol formaldehyde resins, as a non-limiting example, tend not to adhere well to polyester fibers, whereas plasticized vinyl resin in combination with a polymerized amine-formaldehyde derivative have been found to demonstrate greater adhesion to polyester. An ordinary skilled artisan having the benefit of this disclosure would be able to select the type of binder and amount of binder to dispose in a nonwoven web to achieve either lesser or greater extensibility in strength.

Solvent bonding may be used as a bonding technique when the materials of the fibers of the nonwoven web are susceptible to dissolution by the applied solvent. The extent of solvent applied in addition to the characteristics of the materials of the fiber of the nonwoven webs themselves may be determinative of the relative extent of bonding, according to embodiments of the invention encompassing these bonding techniques.

Mechanical bonding, according to certain embodiments of the invention, enmeshes and/or entangles fibers to impart strength to the web. The extent of bonding in nonwoven webs that have been bonded using mechanical bonding depends upon the type of mechanical bonding technique which is used where non-limiting examples include hydroentanglement, needlepunching, and stitchbonding.

In certain exemplary embodiments of the invention, one or more of the nonwoven webs of the hydroentangled composites have been bonded using hydroentanglement. The extent of bonding in the nonwoven webs that have been bonded using hydroentanglement may be controlled by the extent of entanglement imparted to the web, which is typically controlled by the velocity and amount of entangling fluid applied to a unit area of the nonwoven web. The extent of bonding experience in a web that has been needlepunched or stitchbonded may be determined by the needlepunches per unit area of the stitchbonds per unit area or even variations in stitching pattern, respectively, according to other embodiments of the invention.

Ultrasonic bonding is similar to thermal bonding in many respects, and the extent of bonding in nonwoven webs that have been ultrasonically bonded may be representative by the same corresponding factors for a nonwoven web that has been thermally bonded. An ultrasonic bonded web is drawn between a "horn," which produces high frequency sound waves, and a rotary calender, which is referred to as the "anvil." The sound energy, which corresponds to the thermal energy in thermal bonding, generates localized heat through mechanical vibration at the embossing points on the calender where the nonwoven web becomes fused.

In certain embodiments of the invention, one or more nonwoven webs of the hydroentangled composite are bonded using a spunlace process. The spunlace process uses fine, high velocity jets of water to impinge upon the nonwoven web causing the impinged fibers of the nonwoven web to curl and entangle about each other. Jets that penetrate the nonwoven web will form an image on the nonwoven web corresponding to a pattern imaged on the forming built. Not only will the volume and velocity of the jets be determinative of the extent of bonding in the nonwoven web, but differing imaged patterns may also impart a desired extent of bonding in the nonwoven web, according to certain embodiments of the invention.

The meltblown process for forming meltblown webs, for example, comprises extruding a thermoplastic resin through a die having a multiplicity of orifices. Convergent streams of hot air, for example, may be used to rapidly attenuate the extruded polymer streams to form fine diameter fibers. High velocity air may be used to dispose the formed fibers onto a collector screen. The fibers in the meltblown web become bonded through a combination of entanglement and cohesive sticking as adjacent fibers cool and become associated throughout various portions of the meltblown web.

The extent of bonding within a meltblown web may be controlled by various different parameters including, but without limitation, and in any combination, the temperature of the extruded resin, the temperature of the hot stream of air used to form the fibers, the velocity of the air used to form the fibers of the meltblown web onto the collector screen, cooling techniques and the speed of cooling of the formed web onto the collector screen, and the diameter of the fibers controlled, for example, by the size of the orifices of the die and other process conditions. According to certain embodiments of the invention, the collector screen itself may be another nonwoven web, for example, a spunbond web in certain embodiments of the invention.

According to certain other embodiments of the invention, finishing treatment of the nonwoven web may be determinative of the extent or level of bonding in the nonwoven web. A useful finishing technique for the hydroentangled composite of the invention includes laminating where the thickness and type of film used for lamination and the way the film is applied may be determinative of the extent of bonding in the nonwoven web. According to certain embodiments of the invention, a surface treatment may be applied to any of the one or more of the nonwoven webs of the hydroentangled composite to impart an improved extent or level of bonding strength in the nonwoven web.

III. Process for Forming a Hydroentangled Composite

In another aspect, the invention provides a process for forming a hydroentangled composite. The process includes providing a nonwoven material comprising at least two nonwoven webs having different bonding levels such that the at least two nonwoven webs include a first nonwoven web having a first nonwoven web bonding level and a second nonwoven web having a second nonwoven web bonding level, and applying at least one jet of fluid directly or indirectly to the first nonwoven web to impart a three-dimensional pattern onto the nonwoven material. In such embodiments of the invention, the second nonwoven web bonding level may be higher than the first nonwoven web bonding level, the second nonwoven web may be positioned directly or indirectly onto an imaging sleeve having a three-dimensional pattern, and the first nonwoven web may be positioned facing at least one fluid jet.

According to certain embodiments of the invention, for instance, the process may further comprise applying a hydrophilic additive. In some embodiments of the invention, for example, applying the hydrophilic additive may comprise melt dispersing the hydrophilic additive. In other embodiments of the invention, for instance, applying the hydrophilic additive may comprise topically applying the hydrophilic additive. According to certain embodiments of the invention, for example, the process may further comprise pre-entangling the at least two nonwoven webs. Further pursuant to such embodiments of the invention, for instance, the at least two nonwoven webs may be pre-entangled via a hydroentangling process.

In accordance with certain embodiments of the invention, for instance, the process may further comprise meltspinning a polymer composition and forming the at least one nonwoven layer. In some embodiments of the invention, for example, the process may further comprise positioning the first surface of the hydroentangled nonwoven fabric directly or indirectly onto an image transfer device having a three-dimensional pattern and applying jets of fluid directly or indirectly to the second surface of the hydroentangled nonwoven fabric to impart a three-dimensional pattern onto the hydroentangled nonwoven fabric. For example, according to certain embodiments of the invention, the image transfer device may comprise one or more drums or even one or more sleeves affixed to a corresponding drum. One or more water jets, for example, high pressure water jets according to an embodiment of the invention, may be applied to a side of the nonwoven opposite to the side contacting the image transfer device. Without intending to be bound by the theory, the one or more water jets and water directed through the nonwoven causes the fibers of the nonwoven to become displaced according to the image on the image transfer device such as the image formed on one or more drums or one or more sleeves affixed to a corresponding drum causing a three-dimensional pattern to be imaged throughout the nonwoven according to such image. Such imaging techniques are further described in, for example, U.S. Pat. No. 6,314,627 entitled "Hydroentangled Fabric having Structured Surfaces"; U.S. Pat. No. 6,735,833 entitled "Nonwoven Fabrics having a Durable Three-Dimensional Image"; U.S. Pat. No. 6,903,034 entitled "Hydroentanglement of Continuous Polymer Filaments"; U.S. Pat. No. 7,091,140 entitled "Hydroentanglement of Continuous Polymer Filaments"; and U.S. Pat. No. 7,406,755 entitled "Hydroentanglement of Continuous Polymer Filaments", each of which are included in their entirety herein by reference.

In accordance with certain embodiments of the invention, for example, at least one of the first nonwoven web and the second nonwoven web may comprise a spunbond. In certain embodiments of the invention, for instance, the first nonwoven web may comprise a spunbond and the second nonwoven web may comprise a spunbond. In some embodiments of the invention, for example, the spunbond may comprise at least one of a polyolefin, a polyester, or combinations thereof. In further embodiments, for instance, the spunbond may comprise at least one of a polypropylene, a polyethylene, a polyester, or combinations thereof. In other embodiments of the invention, for example, the spunbond may comprise a polypropylene. In such embodiments of the invention, for instance, the spunbond may comprise an isotactic polypropylene. In certain embodiments of the invention, for example, the spunbond may comprise a polyethylene. Further pursuant to such embodiments of the invention, for instance, the spunbond may comprise high density polyethylene ("HDPE"), low density polyethylene ("LDPE"), linear low density polyethylene ("LLDPE"), a copolymer of ethylene and any combination thereof.

According to certain embodiments of the invention, for example, the first nonwoven web and/or the second nonwoven web may comprise one or more bicomponent fibers. Further pursuant to such embodiments of the invention, for instance, the bicomponent fibers may comprise a sheath comprising polyethylene and a core comprising at least one of polypropylene or polyester. In further embodiments of the invention, for example, the first nonwoven web may comprise bicomponent fibers and the second nonwoven web may comprise a polypropylene spunbond. In certain embodiments of the invention, for example, the first nonwoven web may comprise a polypropylene spunbond and the second nonwoven web may comprise bicomponent fibers.

According to certain embodiments of the invention, for example, the hydroentangled composite may comprise more than two nonwoven webs. Exemplary configurations include, but are not limited to, $S_1S_1S_2$, $S_1S_1S_2S_2$, and $S_1S_2S_2$, where $S_1$=the first nonwoven web and $S_2$=the second nonwoven web. In further embodiments, for instance, at least one of the first nonwoven web or the second nonwoven web may comprise an SMS configuration, where S=spunbond and M=meltblown. In other embodiments, for example, at least one of the first nonwoven web or the second nonwoven web may comprise a laminate. In such embodiments, for instance, the laminate may comprise a meltblown layer captured between two layers of continuous filaments or multiple layers of continuous filaments (e.g., spunbond).

In accordance with certain embodiments of the invention, for example, the hydroentangled composite may be abrasion-resistant. In some embodiments, for instance, the hydroentangled composite of the invention may be absorbent. According to certain embodiments, for example, the hydroentangled composite of the invention may have low linting. In such embodiments, for instance, the hydroentangled composite of the invention may have a lint level from about 2 gsm to about 8 gsm. In further embodiments, for example, the hydroentangled composite of the invention may have a lint level from about 2.5 gsm to about 6 gsm. In other embodiments, for instance, the hydroentangled composite of the invention may have a lint level from about 2.8 gsm to about 5 gsm. As such, in certain embodiments, the hydroentangled composite of the invention may have a lint level from at least about any of the following: 2, 2.25, 2.5, 2.75, and 2.8 gsm and/or at most about 8, 7, 6, 5.5, and 5 gsm (e.g., about 2.25-6 gsm, about 2-5 gsm, etc.).

According to certain embodiments of the invention, the hydroentangled composite may have a lint ratio between the second nonwoven web and the first nonwoven web from about 0.1 to about 0.9. In certain embodiments of the invention, the hydroentangled composite may have a lint ratio between the second nonwoven web and the first nonwoven web from about 0.1 to about 0.75. In further embodiments, for example, the hydroentangled composite of the invention may have a lint ratio between the second nonwoven web and the first nonwoven web from about 0.15 to about 0.6. In other embodiments, for instance, the hydroentangled composite of the invention may have a lint ratio between the second nonwoven web and the first nonwoven web from about 0.2 to about 0.5. As such, in certain embodiments, the hydroentangled composite of the invention may have a lint ratio between the second nonwoven web and the first nonwoven web from at least about any of the following: 0.1, 0.12, 0.15, 0.18, and 0.2 and/or at most about 0.9, 0.85, 0.8, 0.75, 0.7, 0.6, 0.55 and 0.5 (e.g., about 0.12-0.55, about 0.1-0.5, etc.).

In accordance with certain embodiments of the invention, for example, the hydroentangled composite may comprise a weighted lint ratio between the second nonwoven web and the first nonwoven web prior to being hydroentangled together comprises less than 0.9, less than 0.8, or less than 0.7. In certain embodiments of the invention, for instance, the hydroentangled composite may comprise a weighted lint ratio between the second nonwoven web and the first nonwoven web prior to being hydroentangled together comprising from at least about any of the following: 0.1, 0.15. 0.2, 0.25, 0.3, 0.35, and 0.4 and/or at most about 0.95, 0.9, 0.85, 0.8, 0.75, 0.7, 0.65, 0.6, 0.55, 0.5, and 0.45 (e.g., about 0.3-0.9, about 0.4-0.9, etc.)

In accordance with certain embodiments of the invention, for example, the hydroentangled composite may have a basis weight from about 10 gsm to about 90 gsm. In further embodiments, for instance, the hydroentangled composite of the invention may have a basis weight from about 20 gsm to about 60 gsm. In other embodiments, for example, the hydroentangled composite of the invention may have a basis weight from about 30 gsm to about 50 gsm. As such, in certain embodiments, the hydroentangled composite of the invention may have a basis weight from at least about any of the following: 10, 15, 20, 25, and 30 gsm and/or at most about 90, 80, 70, 60, and 50 gsm (e.g., about 20-80 gsm, about 10-90 gsm, etc.).

In accordance with certain embodiments of the invention, for instance, the hydroentangled composite may have a strength factor from about 1 N/gsm to about 2 N/gsm. In further embodiments, for example, the hydroentangled composite of the invention may have a strength factor from about 1.25 N/gsm to about 1.75 N/gsm. In other embodiments, for instance, the hydroentangled composite of the invention may have a strength factor from about 1.35 N/gsm to about 1.65 N/gsm. As such, in certain embodiments, the hydroentangled composite of the invention may have a strength factor from at least about any of the following: 1, 1.25, 1.35, 1.4, and 1.5 N/gsm and/or at most about 2, 1.9, 1.8, 1.75, and 1.65 N/gsm (e.g., about 1.35-1.9 N/gsm, about 1.5-2 N/gsm, etc.).

In accordance with certain embodiments of the invention, for example, the hydroentangled composite may have a three-dimensional pattern. Further pursuant to such embodiments of the invention, for instance, the three-dimensional pattern may comprise substantially parallel ridges and depressions. In certain embodiments of the invention, for example, the three-dimensional pattern may comprise a zigzag pattern.

FIG. 6, for example, illustrates a process flow diagram for forming a hydroentangled composite according to an embodiment of the invention showing optional steps of pre-entangling at least two nonwoven webs and applying a hydrophilic additive to the hydroentangled composite. As shown in FIG. 6, the exemplary process includes optionally pre-entangling at least two nonwoven webs at operation 410, providing a nonwoven material comprising at least two nonwoven webs having different bonding levels such that the at least two nonwoven webs include a first nonwoven web having a first nonwoven web bonding level and a second nonwoven web having a second nonwoven bonding level at operation 420, applying at least one jet of fluid directly or indirectly to the first nonwoven web to impart a three-dimensional pattern onto the nonwoven material at operation 430, and optionally applying a hydrophilic additive at operation 440.

Thus, the invention includes, according to certain embodiments, a hydroentangled composite based, at least in part, on at least two nonwoven webs, such that the hydroentangled composite has a three-dimensional structure, and the at least two nonwoven webs have different bonding levels. Hydroentangled composites, according to certain embodiments of the invention, may exhibit better separation, softness, low linting, and good fluid handling characteristics (e.g., acquisition rate and rewet)

EXAMPLES

The present disclosure is further illustrated by the following examples, which in no way should be construed as being limiting. That is, the specific features described in the following examples are merely illustrative and not limiting.

Test Methods

Basis weight of the following examples was measured in a way that is consistent with the ASTM test method D3776. The results were provided in units of mass per unit area in g/m$^2$ (gsm).

The strip tensile strength of the web is measured according to ASTM test method D5035.

Linting measured the tendency of a web to shed particles when a roller with adhesive tape is rolled against it. The method used is WSP 400.0 (05) with a few modifications. The key modifications are described below:

A) The apparatus used to move consistently and repeatably the roller with the double side tape over the piece of fabric is the Peter Viehoever Uberroller, Model RDG-03 (Manufactured by Peter Viehoever Sondermachinen, Kaarst-Buttgen, Germany). The travel length setting was 150. The test may also include consistently and repeatably moving the roller across the web more than once with each movement back and forth being characterized as a cycle. The linting data included in the examples has been measured using five (5) cycles.

B) The two-side adhesive tape used was 3M model 415 (Manufactured by 3M, MN, USA).

C) Only six 75×425 mm pieces were taken per samples with the long direction of the pieces running parallel with the machine direction (MD) of the web (No samples with the long direction parallel to the cross direction of the web were taken and tested).

D) The lint results reported were the average of the Side A and Side B results for the six pieces taken from the sample. The WLL was calculated from this average and the average of the basis weight for the sample.

Caliper was measured using a Progauge model 89-2009 sold by Thwing-Albert Instrument Company, West-Berlin, N.J., USA. The results were report in mm.

Air permeability data were produced using a TexTest FX3300 Air Permeability Tester manufactured by TexTest AG of Zurich, Switzerland. The TexTest FX3300 Air Permeability Tester was used in accordance with the manufacturer's instructions using a 38 $cm^2$ orifice and a pressure drop of 125 Pa as per test method WSP 70.1. The results were recorded in the units of $cm^3/cm^2/sec$.

Strike through and rewet data were obtained by testing the samples as per EDANA/INDA Worldwide Strategic Partners standard tests WSP 70.7 (05) "Standard Test Method for Nonwovens-Repeat Liquid Strike-Through time" ("WSP 70.7") and 70.8 (05) "Standard Test Method for Wetback After Repeated Strike-Through Time" ("WSP 70.8"). The WSP 70.7 tests were performed using a Lister AC by Lenzing Instruments GmbH & Co KG, Lenzing, Austria. For the WSP 70.7 test method, the strike through time for insult of 5 ml of a 0.9% saline solution was recorded in seconds after the first, second and third insult. After performing the WSP 70.7 test on a sample, rewet was measured in accordance with WSP 70.8. For the WSP 70.8 test method, the WetBack testing unit from Lenzing Instruments GmbH & Co was used. Paper used for the absorbent core was type ERT FF3 supplied by Hollingworth & Vose, Winchcombe, England. The filter paper used for rewet test was the type ERTMWWSSHEETS, 125 mm (UPC 0041729020442) also from Hollingworth & Vose.

Example 1

In Example 1, spunbond samples were produced. All samples were produced on a 2-beam Reicofil®-2 spunbond line (Reifenhtuser Reicofil, Spicher Straβe 46, 53844 Troisdorf, Germany) fitted with a point bond calender. The pattern for the embossed calender roll was a typical diamond bonding pattern having a bonding area between 14 and 19%.

All the 10 gsm spunbond samples were produced using the same extruding and spinning conditions and a 35 MFR polypropylene. The only difference between the samples was the set points for the oil heating the calender rolls, which were varied by increments of about 5 to 6° C. In this regard, it was observed that the lowest temperature selected was closer to the optimal temperature for tensile properties of the series, and the highest temperature selected was the temperature that produced the lowest lint results. As noted previously, the lint results are based on subjecting the samples to five (5) cycles in accordance with the modified-WSP 400.0(05) method described above.

TABLE 1

| Sample | Temperature set-points for the calender roll oil Top/bottom (° C.) | Basis weight gsm | Air permeability $cm^3/cm^2/sec$ | Average lint $g/m^2$ | Weighted Lint Level (WLL) for basis weight $g^2/m^4$ | MD Strip Tensile Strength N/5 cm | CD Strip Tensile Strength N/5 cm | Strength Factor N/(5 cm * gsm) |
|---|---|---|---|---|---|---|---|---|
| A | 141/146 | 10.3 | 563 | 0.46 | 4.74 | 27.3 | 13.3 | 3.94 |
| B | 146/152 | 10.5 | 570 | 0.42 | 4.41 | 27.0 | 12.3 | 3.74 |
| C | 152/157 | 10.3 | 552 | 0.18 | 1.85 | 24.2 | 12.1 | 3.52 |
| D | 146/152 | 19.9 | 330 | 0.19 | 3.78 | 45.0 | 25.0 | 3.52 |
| E | 152/157 | 19.7 | 349 | 0.1 | 1.97 | 44.1 | 24.8 | 3.50 |
| F | 157/163 | 19.9 | 325 | 0.08 | 1.59 | 41.1 | 22.1 | 3.18 |

The samples made at 20 gsm were produced using the same polymer as well as using the same extruding and spinning conditions as for the 10 gsm samples, however the collection belt speed was reduced to produce the higher basis weight, and the range of set point temperatures for the oil heating the calender rolls was adjusted to reflect the higher basis weight. Again, the increments between adjacent bonding set points were about 6° C. apart, and the lowest temperature used was the temperature producing the most optimal tensile properties of the series, while the highest temperature produced the lowest lint.

The bonding conditions as well as the test results for the 10 gsm samples (Samples A-C) and the 20 gsm samples (Samples D-F) can be found in Table 1. As shown in Table 1, the highest tensile strength did not correspond to the lowest lint level measured in a series.

Example 2

In Example 2, Samples A-C and D-F were combined by hydroentangling on the pilot line one web taken from the Samples A-C series and one web taken from the Samples A-C or Samples D-F series. The pilot line included a first section where the two spunbond webs were pre-entangled while traveling on top of a belt in a flat section of the line. For these pre-entangled spunbond webs, four sets of water jets were used with pressures set in a progressing order of 13.8, 27.6, 55.2 and 68.9 Bars. The pre-entangled web was then moved to a 3D imaging sleeve where two injectors were used at 117 Bars. Suitable 3D imaging sleeves according to certain embodiments of the invention include those described, for example, in RE38,105 and RE38,505, in which the contents of both are hereby incorporated by reference in their entirety. The sleeve used was a zigzag-patterned sleeve. After entangling, the composite was dried using banks of steam cans. Because the pilot line was narrow and long, neck-in of the product occurred that translated into an increase in basis weight when compared to the precursor webs. This effect was typically more pronounced for the lighter and less bonded webs.

Table 2 shows the construction of the samples as well as the basis weight, thickness and tensile properties.

TABLE 2

| Sample | SB facing the water jets (nominal basis weight in g) | SB facing the imaging sleeve (nominal basis weight in g) | Basis weight Gsm | Caliper mm | MD Strip tensile strength N | CD Strip tensile strength N | Strength factor N/gsm |
|---|---|---|---|---|---|---|---|
| 1 | A (10) | A (10) | 30.4 | 0.44 | 36.5 | 7.36 | 1.44 |
| 2 | C (10) | C (10) | 26.4 | 0.36 | 27.4 | 6.14 | 1.27 |
| 3 | A (10) | C (10) | 27.0 | 0.38 | 32.8 | 9.67 | 1.57 |
| 4 | C (10) | B (10) | 26.7 | 0.39 | 26.8 | 7.26 | 1.28 |
| 5 | B (10) | A (10) | 26.2 | 0.41 | 28.2 | 7.12 | 1.35 |
| 6 | C (10) | F (20) | 32.8 | 0.44 | 35.1 | 11.7 | 1.43 |
| 7 | C (10) | D (20) | 34.5 | 0.49 | 28.8 | 11.1 | 1.16 |
| 8 | B (10) | F (20) | 33.7 | 0.38 | 37.1 | 11.7 | 1.45 |
| 9 | A (10) | E (20) | 33.9 | 0.46 | 34.4 | 11.2 | 1.35 |
| 10 | B (10) | D (20) | 36.1 | 0.47 | 30.7 | 13.1 | 1.21 |

Table 3 shows the linting as well as the strike through and rewet data for the composite samples. As illustrated by Samples 3, 6, 8, and 9, the lowest lint results for the hydroentangled composite were obtained when the web that faced the imaging sleeve (Top web) was the web having the lower lint value of the two webs, and when the ratio of Weighted Lint Level between the precursor webs (top/bottom or imaging tool/water jet) was less than 0.9, and the strength factor of the composite was above 1.3 N/(5 cm*gsm) or, when the ratio of Lint for the precursor web was less than 0.45 and the strength ratio of the composite was above 1.3 N/(5 cm*gsm). As illustrated by Sample 2, combining two webs with low lint performance did not produce the optimum composite in regard to linting. Thus, there appears to be a relationship between lower lint level and higher strength ratio for the composite. This relationship could be due to the improved anchoring of the webs together when the web facing the water jets during imaging were more broken down and the filaments were freer to entangle with the more stable structure of the better bonded web.

Table 4 shows the calculated percentage increase for the extent of additional energy imparted to the bottom nonwoven web relative to the energy imparted to the top nonwoven web assuming that bonding strength between the top and bottom.

TABLE 4

| Sample | $T_{avg,jet}$ °C. | $T_{avg,sleeve}$ °C. | Basis Weight$_{sleeve}$ gsm | Increase in Bonding Energy % | Linting for the Composite g/m² |
|---|---|---|---|---|---|
| 1 | 143.5 | 143.5 | 10 | 0 | 3.82 |
| 2 | 154.5 | 154.5 | 10 | 0 | 4.61 |
| 3 | 143.5 | 154.5 | 10 | 8.5 | 3.51 |
| 4 | 154.5 | 149.0 | 10 | -4.2 | 4.69 |
| 5 | 149.0 | 143.5 | 10 | -4.4 | 5.29 |
| 6 | 154.5 | 160.0 | 20 | 4.2 | 3.10 |
| 7 | 154.5 | 149.0 | 20 | -4.2 | 4.90 |
| 8 | 149.0 | 160.0 | 20 | 8.9 | 3.50 |

TABLE 3

| Sample | SB facing the water jets (Bottom) | SB facing the imaging sleeve (Top) | Basis Weight gsm | Linting for composite g/m² | Ratio of Lint between top & bottom spunbound webs | Ratio of WLL between top & bottom spunbond webs | Linting for the spunbond facing the imaging sleeve and the wearer g/m² | Strike through 1$^{st}$ insult sec | Strike through 2$^{nd}$ insult sec | Strike through 3$^{rd}$ insult sec | Reset 3$^{rd}$ insult grams |
|---|---|---|---|---|---|---|---|---|---|---|---|
| 1 | A | A | 30.4 | 3.82 | 1.00 | 1.00 | 0.46 | 22.3 | 23.2 | 24.5 | 0.12 |
| 2 | C | C | 26.4 | 4.61 | 1.00 | 1.00 | 0.18 | 21.7 | 23.0 | 23.9 | 0.43 |
| 3 | A | C | 27.0 | 3.51 | 0.39 | 0.39 | 0.18 | 24.0 | 23.2 | 25.9 | 0.96 |
| 4 | C | B | 26.7 | 4.69 | 2.33 | 2.38 | 0.42 | 23.3 | 26.4 | 29.7 | 0.24 |
| 5 | B | A | 26.2 | 5.29 | 1.10 | 1.07 | 0.46 | 27.3 | 32.5 | 35.1 | 0.24 |
| 6 | C | F | 32.8 | 3.10 | 0.44 | 0.86 | 0.08 | 31.7 | 32.8 | 35.1 | 0.15 |
| 7 | C | D | 34.5 | 4.90 | 1.06 | 2.04 | 0.19 | 31.0 | 35.9 | 38.9 | 0.10 |
| 8 | B | F | 33.7 | 3.50 | 0.19 | 0.36 | 0.08 | 29.6 | 31.8 | 33.9 | 0.17 |
| 9 | A | E | 33.9 | 2.94 | 0.22 | 0.42 | 0.10 | 26.0 | 27.6 | 29.2 | 0.14 |
| 10 | B | D | 36.1 | 5.54 | 0.45 | 0.86 | 0.19 | 26.1 | 27.7 | 28.9 | 0.15 |

If the amount of heat transferred by the calendar roll to the nonwoven web is deemed proportional to $(T_{avg}-T_{web})$ and $T_{avg}$ is the average oil temperature between the top and bottom calendar roll for the corresponding spunbond and $T_{web}$ is assumed to be approximately 25° C., the temperature of the web, then the percentage change in the extent of bonding level based upon the difference in the amount of energy transferred between the spunbond facing the water jets and the spunbond facing the imaging sleeve may be approximated by equation 1.

% Increase = $100 \times (T_{avg,jet} - T_{avg,sleeve})/(T_{avg,jet} - 25)$ (1)

TABLE 4-continued

| Sample | $T_{avg,jet}$ °C. | $T_{avg,sleeve}$ °C. | Basis Weight$_{sleeve}$ gsm | Increase in Bonding Energy % | Linting for the Composite g/m² |
|---|---|---|---|---|---|
| 9 | 143.5 | 154.5 | 20 | 9.3 | 2.94 |
| 10 | 149.0 | 149.0 | 20 | 0 | 5.54 |

FIGS. 7A and 7B show the percentage increase in bonding energy between the spunbond facing the imaging sleeve and the spunbond facing the water jets plotted against the linting for the composite for the spunbond facing the water jet having a basis weight of 10 gsm and 20 gsm, respectively. The correlation coefficient for the % increase in bonding energy between the spunbond facing the water jets and the spunbond facing the imaging sleeve is −0.85 for the spunbond facing the imaging sleeve having a basis weight of 10 gsm and −0.81 for spunbond facing imaging sleeve having a basis weight of 20 gsm. This suggests that an increasing amount of bonding energy for the spunbond facing the water jets compared to the bonding energy for the spunbond facing the imaging sleeve results in a reduction in the amount of linting for the composite.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A hydroentangled composite comprising:
   at least two thermally bonded nonwoven webs hydroentangled together and comprising a first nonwoven web defining a first outer surface of the hydroentangled composite and a second nonwoven web defining a second outer surface of the hydroentangled composite, wherein at least the first nonwoven web comprises a spunbond, and each of the first outer surface and the second outer surface being defined by a three-dimensional pattern imparted therein, and
   wherein a weighted linting level (WLL) ratio between the second nonwoven web and the first nonwoven web prior to being hydroentangled together comprises a value of less than 0.9, and where WLL is defined as follows—

$WLL=(L*BWt)$;

wherein (i) 'L' is the linting level for a given nonwoven web as determined by WSP 400.0 (05) modified by using a travel setting of 150 and a sample size of 75×425 mm in which the linting level is an average value for the first outer surface and the second outer surface ("modified WSP"), and (ii) 'BWt' is the basis weight of the given nonwoven web as determined by ASTM D3776;
   wherein the first nonwoven web has been thermally bonded at a first thermal bonding energy defining a first plurality of discrete thermal bonds and the second nonwoven web has been thermally bonded at a second thermal bonding energy defining a second plurality of discrete thermal bonds prior to being hydroentangled together, and the second thermal bonding energy is at least 5% greater than the first thermal bonding energy;
   wherein the first nonwoven web and the second nonwoven web each comprises at least one of a polyolefin, a polyester, or combinations thereof;
   wherein the hydroentangled composite has a strength factor (SF) from 1.5 to 2.0 N/gsm, wherein 'SF' is the sum of strip tensile strengths of the hydroentangled composite in the machine direction (TS1) and cross direction (TS2) divided by a basis weight of the hydroentangled composite;
   wherein the hydroentangled composite further comprises a linting level for the composite of 2 $g/m^2$ to 3.51 $g/m^2$ as determined by WSP 400.0 (05) modified by using a travel setting of 150 and a sample size of 75×425 mm in which the linting level is an average value for the first outer surface of the hydroentangled composite and the second outer surface of the hydroentangled composite;
   wherein the first nonwoven web and the second nonwoven webs are hydroentangled together by having the first nonwoven web positioned directly facing at least one fluid jet and the second nonwoven web is adjacent an imaging sleeve, and
   wherein the hydroentangled composite is consolidated by only the first plurality of discrete thermal bonds, the second plurality of discrete thermal bonds, and a plurality of hydroentangled fibers.

2. The hydroentangled composite according to claim 1, wherein the WLL ratio comprises a value between 0.3 and 0.9.

3. The hydroentangled composite according to claim 2, wherein the first nonwoven web comprises a spunbond and the second nonwoven web comprises a spunbond.

4. The hydroentangled composite according to claim 1, wherein the first nonwoven web and the second nonwoven web each comprise a polypropylene.

5. The hydroentangled composite according to claim 1, wherein at least one of the first nonwoven web, the second nonwoven web, or both comprise bicomponent fibers.

6. The hydroentangled composite according to claim 5, wherein the bicomponent fibers comprise a sheath comprising polyethylene and a core comprising at least one of a polypropylene or a polyester.

7. The hydroentangled composite according to claim 1, wherein the three-dimensional pattern comprises substantially parallel ridges and depressions.

8. The hydroentangled composite according to claim 1, wherein the three-dimensional pattern comprises a zigzag pattern.

9. The hydroentangled composite according to claim 1, wherein the hydroentangled composite comprises a lint ratio between a second nonwoven web lint level and a first nonwoven web lint level from about 0.1 to about 0.75; wherein lint level for a given nonwoven web is determined by WSP 400.0 (05) modified by using a travel setting of 150 and a sample size of 75×425 mm in which the linting level is an average value for the first outer surface and the second outer surface.

10. A hydroentangled composite, comprising:
    at least two nonwoven webs hydroentangled together, including a first nonwoven web defining a first outer surface of the hydroentangled composite and a second nonwoven web defining a second outer surface of the hydroentangled composite; wherein the first nonwoven web and the second nonwoven web each comprises at least one of a polyolefin, a polyester, or combinations thereof;
    said first nonwoven web comprising a first lint level prior to hydroentanglement and said second nonwoven web comprising a second lint level prior to hydroentanglement, wherein the first lint level is greater than the second lint level and a first thermal bonding energy is less than the second thermal bonding energy; wherein the first lint level and the second lint level are each determined by WSP 400.0 (05) modified by using a travel setting of 150 and a sample size of 75×425 mm in which the linting level is an average value for the first outer surface and the second outer surface ("modified WSP");

each of said first outer surface and said second outer surface of the hydroentangled composite defined by a three-dimensional pattern imparted into the hydroentangled composite;

wherein the first nonwoven web has been thermally bonded at a first thermal bonding energy defining a first plurality of discrete thermal bonds and the second nonwoven web has been thermally bonded at a second thermal bonding energy defining a first plurality of discrete thermal bonds prior to being hydroentangled together, and the second thermal bonding energy is from 5% to 20% greater than the first thermal bonding energy;

wherein the hydroentangled composite has a strength factor (SF) from 1.5 N/gsm to 1.775 N/gsm; wherein 'SF' is the sum of strip tensile strengths of the hydroentangled composite in the machine direction (TS1) and cross direction (TS2) divided by a basis weight of the hydroentangled composite;

wherein the hydroentangled composite further comprises a linting level for the composite of 2 g/m² to 3.51 g/m² as determined by WSP 400.0 (05) modified by using a travel setting of 150 and a sample size of 75×425 mm in which the linting level is an average value for the first outer surface of the hydroentangled composite and the second outer surface of the hydroentangled composite, and wherein the hydroentangled composite is consolidated by only the first plurality of discrete thermal bonds, the second plurality of discrete thermal bonds, and a plurality of hydroentangled fibers.

11. The hydroentangled composite according to claim 10, wherein a weighted linting level (WLL) ratio between the second nonwoven web and the first nonwoven web prior to being hydroentangled together comprises from about 0.3 to about 0.9; wherein WLL is defined as follows—

$$WLL=(L*BWt);$$

wherein (i) 'L' is the linting level for a given nonwoven web, and (ii) 'BWt' is the basis weight of the given nonwoven web as determined by ASTM D3776.

12. The hydroentangled composite according to claim 1, wherein the hydroentangled composite further comprises a linting level for the composite of 2.94 g/m² to 3.51 g/m² as determined by WSP 400.0 (05) modified by using a travel setting of 150 and a sample size of 75×425 mm in which the linting level is an average value for the first outer surface of the hydroentangled composite and the second outer surface of the hydroentangled composite.

13. The hydroentangled composite according to claim 12, wherein the second thermal bonding energy is from 8.5% to 9.3% greater than the first thermal bonding energy.

14. The hydroentangled composite according to claim 10, wherein the first nonwoven web and the second nonwoven webs are hydroentangled together by having the first nonwoven web positioned directly facing at least one fluid jet and the second nonwoven web is adjacent an imaging sleeve.

* * * * *